United States Patent [19]

Fischer

[11] Patent Number: 4,836,217

[45] Date of Patent: Jun. 6, 1989

[54] HYPERSENSITIVITY TEST MEANS

[76] Inventor: Torkel I. Fischer, Rosenvägen 57, S-752 52 Uppsala, Sweden

[21] Appl. No.: 871,420

[22] PCT Filed: Sep. 23, 1985

[86] PCT No.: PCT/SE85/00361

§ 371 Date: Apr. 11, 1986

§ 102(e) Date: Apr. 11, 1986

[87] PCT Pub. No.: WO86/01994

PCT Pub. Date: Apr. 10, 1986

[30] Foreign Application Priority Data

Oct. 1, 1984 [SE] Sweden .................................. 8404895

[51] Int. Cl.$^4$ .............................................. A61B 15/00
[52] U.S. Cl. ...................................... 128/743; 424/449
[58] Field of Search ............... 128/743, 632, 636, 760, 128/762, 771; 424/447–449

[56] References Cited

U.S. PATENT DOCUMENTS

| | | |
|---|---|---|
| 3,419,006 | 12/1968 | King . |
| 3,507,269 | 4/1970 | Berry .................................. 128/636 |
| 3,515,126 | 6/1970 | Fregert ................................ 128/743 |
| 3,552,929 | 1/1971 | Fields et al. ................... 128/632 X |
| 3,703,890 | 11/1972 | Saunders, Jr. . |
| 3,742,951 | 7/1973 | Zaffaroni . |
| 3,797,494 | 3/1974 | Zaffaroni . |
| 3,894,531 | 7/1975 | Saunders, Jr. . |
| 3,900,027 | 8/1975 | Keedwell ......................... 128/156 X |
| 3,996,934 | 12/1976 | Zaffaroni . |
| 4,014,334 | 3/1977 | Theeuwes et al. . |
| 4,083,974 | 4/1978 | Turi ..................................... 424/241 |
| 4,158,359 | 6/1979 | Kurokawa et al. ................. 128/630 |
| 4,214,592 | 7/1980 | Jacquet et al. ...................... 128/743 |
| 4,304,591 | 12/1981 | Mueuer et al. ................. 424/449 X |
| 4,390,027 | 6/1983 | Alani et al. ......................... 128/743 |
| 4,444,193 | 4/1984 | Fogt .................................. 128/636 X |
| 4,450,844 | 5/1984 | Quisno ................................. 128/743 |
| 4,472,507 | 9/1984 | Pluim, Jr. ....................... 128/743 X |
| 4,595,011 | 6/1986 | Phillips ........................... 128/760 X |
| 4,675,009 | 6/1987 | Hymes et al. .................. 424/449 X |

FOREIGN PATENT DOCUMENTS

| | | |
|---|---|---|
| 0043047 | 5/1985 | Australia . |
| 0043878 | 5/1985 | Australia . |
| 8320480.6 | 11/1983 | Fed. Rep. of Germany . |
| 0064613 | 4/1982 | Japan .................................. 128/743 |
| 0112323 | 7/1982 | Japan .................................. 128/743 |
| 1459262 | 12/1976 | United Kingdom . |

OTHER PUBLICATIONS

Beecham Group Ltd.; Testing the Supersensitivity of the Skin 5/1968.
Contact Dermatitis 3 (1965) 66–8, Allergic Contact Dermatitis from Povidone–Iodine.
Contact Dermatitis 11 (1984) pp. 137–140, 224–228 and 285–287 and 12 (1985) pp. 12–14 and 200–202.
Seminars in Dermatology, vol. 5, No. 3 (Sep. 1986, pp. 214–224, Patch testing in allergic contact dermatitis; An update.
British Journal of Dermatology 112 (1985) pp. 63–68 by Maibach & Fischer, The thin layer rapid use epicutaneous test (TRUE-test) a new etc.
Brochure on Finn Chamber (Epitest Ltd Oy P O Box 943, SF–00101 Helsinki Finland).
British Journal of Dermatology III (1984) Supplement 27, iii pp. 163–167.
Neotest, Institute Merieux Intl, Merial S.A. 17, Rue Bourgelat 69002 Lyon France.
Farmdoc Complete Specifications Book No. 737 5-2-1-68 Derwent Publications Ltd London.
Accession No. 31888 (Prov A35) Central Patent Index Section B.
Contact Dermatitis; Churchill Livingstone; Edinburgh, London & NY 1980, p. 17.
Fischer, T. I. & Maibach, H. I., British Journal of Dermatology 112 (1985) pp. 63–68.
Pirila, W et al, Proceedings of the XV Intl Congress of Dermatology, Mexico, Oct. 16–21, 1977 803–804.
Pirila, W. et al, Acta Dermatol. Venerol. 47 (1967) pp. 419–425.
Miller, M. V. The Pfizer Text Handbook of Microbial Metabolites McGraw-Hill Book Co Inc NY Toronto London.
J. Am Acad Dermatol. 6 (1982) 473–5.
Allergic Contact Dermatitis to Povidone–Iodine.

Primary Examiner—Kyle L. Howell
Assistant Examiner—Angela D. Sykes
Attorney, Agent, or Firm—Fred Philpitt

[57] ABSTRACT

The invention relates to a novel device and method for carrying out occlusive epicutaneous tests (patch tests). This type of test is employed for detecting contact allergy to some specific substance (allergen) or for testing allergenic and/or irritant properties of a substance. The invention is characterized in that the test substance is incorporated in a dry film.

12 Claims, No Drawings

HYPERSENSITIVITY TEST MEANS

This invention relates to a novel means for carrying out occlusive epicutaneous tests (patch tests). This type of test is employed for detecting contact allergies (contact sensitization) to some specific substance (allergen) or for testing allergic and/or irritant properties of a substance. For the sake of simplicity, the method of this invention is called "My Test".

The term "patch test" derives from the fact that initially patches of fabric or paper were used for carrying out the tests, these patches being soaked with the substance to be tested. During the years many different types of patches have been employed. In connection with the invention the term patch primarily denotes the area carrying the test substance.

In the epicutaneous testing procedure, the substance suspected to have allergenic or irritant properties is applied to normal skin under occlusion for a certain period of time, this application being effected in a controlled manner and with a suitable formulation and concentration of the test substance. This will then, in contact allergy cases, produce an allergic eczema in the test area. Irritant substances give rise to irritative eczema reactions of a similar character (Manual of Contact Dermatitis; Fregert S, 2nd ed. Munksgaard, Copenhagen /1981/ p. 71-76). Usually the test substance is applied in a suitable vehicle, as a rule petrolatum or water. The "patches" in the patch test method are nowadays usually small cup of alumnium foil which when the test is to be carried out are filled with a suitably formulated preparation of the test substance and applied in a manner such that the test will be performed under occlusion. Often a plurality of patches are affixed to an adhesive tape covered with a detachable protective foil.

The methods and materials commonly employed for patch tests are unsatisfactory in respect of safety requirements; this applied especially to methods and materials used for metal salts. Improvements are therefore desirable. Cp. Kalimo, K. et al., Concact Dermatitis 10 (1984), p. 25-29: Schmidt H. et al., Contact Dermatitis 6 (1980), p. 91-94. In allergy testing procedures irritative reactions are common, in particular if the test substances are employed in concentrations close to their thresholds of irritancy. At least in part this is due to the fact that the test substances are not evenly distributed over the skin contact area. Microscopic examinations of standard patch test material have shown that most of the allergens when incorporated in the recommended petrolatum vehicles are dispersed unevenly therein, either in the form of particles or as droplets of varying size (Vannestre D. et al., Contact Dermatitis 6 (1980), p. 197-203; Fossereau J. et al., Occupational Contact Dermatitis. Munksgaards, Copenhagen /1982/, p. 45). The largest of these inclusions measure more than 0.5 mm in diameter. Such particles when dissolving in sweat produce a high local concentration of the allergen and cause pore inflammations ("poritis") around hair follicles. Another disadvantage is that the amount of test substance applied in a standard patch test may vary within a sixth-power range (Fisher T. et al., Contact Dermatitis 1 /1984/, p. 285-87). All this shows that it is highly desirable to achieve improvements in the pharmacological properties of materials to be employed in patch test procedures.

My test solves many of the aforesaid problems, in that it gives an accurate dosage, uniform surface distribution and high bioavailability of the test substance. My test thus offers a solution to such problems of low bioavailability, uncertain dosage and uneven surface distribution as may easily arise when petrolatum is employed as the vehicle.

The present invention provides methods applicable to occlusive patch test techniques, said methods (a) minimizing the required amount and increasing the dosage precision of the test substance (does per unit area), (b) permitting the manufacture of test preparations which are stable in storage, and (c) permitting prefabricated test strips to be made each containing a plurality of test substance preparations, with little risk of mutual cross contamination.

It has to be pointed out that My test must not be confused with non-occlusive techniques of various kinds. In occlusive techniques, the contact between the test substance and skin takes place in an enclosed space; this means that air and its humidity are excluded, with simultaneous inclusion of moisture (sweat) from the test skin area together with the test substance. To achieve this a sealing material is used, e.g. an aluminum foil or an impervious plastics foil. This closed space procedure makes the occlusive technique easy to standardize and has proved to give reliable results (Pirila V, Contact Dermatitis 1 /1975/ p. 48-52). Film-forming polymers have been employed earlier in non-occlusive techniques (see Accession Number 31888 /prov A358/ Central Patents Index Section B, Farmdoc, Derwent Publications Ltd, London 1968).

According to the invention, the aforesaid problems are solved by the use of a patch which is substantially impermeable to moisture and water and on which the test substance is incorporated in a vehicle consisting of a thin supple film in which the test substance is uniformly distributed. This patch will be named "film carrier" hereinafter. The term "supple" means that the film is not so brittle as to crack when employed in My test. At the time when it is to be used the film should be sufficiently dry and hydrophilic to be capable of absorbing excretion products from the skin while being applied to the skin under occlusive conditions.

A layer in order to be properly regarded as a "film" ought to have a thickness of less than 0.25 mm (0.01 inch), see Encyclopedia of Polymer Science and Technology, Plastics, Resins, Rubbers, Fibers, Vol. 6 p. 764 (1967); John Wiley & Sons Inc., USA. The invention thus in its preferred embodiments employs films having a thickness of less than 0.25 mm, preferably less than about 0.1 mm, e.g. less than about 0.05 mm. These thickness values refer to the film prior to its application to the skin, that is, prior to the stage in which it has adsorbed anything from the skin. The film area on each patch may be subdivided into partial areas, although preferably the film area is coherent all over.

TEST SUBSTANCES

The invention is useful in the first place for detecting contact allergies, and the test substances are therefore chosen mainly from among those allergens that cause or are suspected to cause such allergies; but also irritant substances may be used. Potentially all and any kinds of contact allergens and irritant substances can be employed in accordance with this invention, irrespective of whether they are to be classified as solid or liquid substances, organic or inorganic substances, metal salts or non metal salts, soluble or insoluble (in e.g. water).

To facilitate work with patch testing, the most common allergens in different geographical regions have been selected for each respective region. Thus for North America there is a standard "tray" (list) compiled in 1984 by the American Academy of Dermatology and consisting of the following: Benzocain (5 % petrolatum), imidazolidinyl urea (2 % aq), Thiuram mix (1 % petrolatum), cinnamic alcohol (5 % petrolatum) dibucaine (1 % petrolatum), mercaptobenzothiazole (1 % petrolatum), neomycin sulfate (20 % petrolatum), p-phenylenedimine (1 % petrolatum), tetracaine (1 % petrolatum), p-tert.butylphenol formaldehyde resin (1 % petrolatum), Thiomersal (0.1 % petrolatum), formaldehyde (2 % aq.), hydroxycitronellal (4 % petrolatum), Carba mix (3 % petrolatum), cinnamic aldehyde (2 % petrolatum), rosin (colophony) (20 % petrolatum), PPD mix (black rubber mix) (0.6 % petrolatum), wool (lanolin) alcohols (30 % petrolatum), cyclomethycaine (1 % petrolatum), eugenol (4 % petrolatum), Quaternium-15 (2 % petrolatum), isoeugenol (4 % petrolatum), mercapto mix (1 % petrolatum), epoxy resin (1 % petrolatum), potassium dichromate (0.5 % petrolatum), caine mix less benzocaine (3 % petrolatum), ethylenediamine dihydrochloride (1 % petrolatum), benzoyl peroxide (1 % petrolatum), balsam of Peru (25 % petrolatum), Quaternium-15 (2 % aq.), oak moss (abs. mousse de chene) (5 % petrolatum), nickel sulfate (2.5 % petrolatum). For Europe the recommended 1984 tray comprised the following list (for the sake of simiplicity, concentrations and vehicles are omitted here): Neomycin sulfate, potassium dichromate, wool alcohols, mercapto mix, benzocaine, nickel sulfate, epoxy resins, ethylenediamine dihydrochloride, cobalt chloride, balsam of Peru, Thiuram mix, parabenes (mix), p-phenylenediamine dihydrochloride, colophony, quinoline mix, black rubber mix, p-tert.butylphenol formaldehyde resin, Carba mix, mix of fragrances, Quaternium-15, primine, formaldehyde. Also there are standard trays for contact dermatitis conditions on various parts of the body, e.g. for dermatitis on the lower portion of the leg: Neomycin sulfate, qunioform, benzocaine, wool alcohols, balsam of Peru, chloroquinaldol, parabenes (mix), anhydrous eucerine, colophony.

These so-called "standard allergens" are employed on most of the patients. Often also the patient's clinical history is referred to for deciding what further allergens are to be included in specifically his/her test series. There are a further c. 2 000 known allergens that may conceivably be of interest for the patch testing procedure.

According to the invention, the test substance is incorporated in a homogeneous supple solid phase in which said substance is present optionally in a microparticulate form. The particle size in the film plane is less than 100 /μm, for instance less than 50 /μm. At right angles to the film plane, the particle size may be less than 10 /μm, for instance less than 5 /μm.

VEHICLE

The vehicle will be selected from among substances having film-forming properties. Usually it is a polymer which together with a volatile liquid such as e.g. water will give a gel or coalescible emulsion in which the test substance chosen can be distributed homogeneously in a dissolved, crystallized, micronized, emulsified or dispersed state; in the most practical embodiment of the invention, this polymer is chosen such that its gel or emulsion when spread out can dry to form a film. The vehicle should have hydrophilic properties so that it will absorb moisture when in use.

Information as to various characteristics revealing the hydrophilic properties of a vehicle is available from handbooks and from producers, see for example Encyclopedia of Polmer Science and Technology, Plastics, Rubbers, Resins, Fibers; John Wiley & Sons Inc., Vol 6 p. 778–779 (1967). Suitable polymers will be found among those that have a water adsorption value (24h) exceeding 0.5 %, preferably exceeding 1 % (as measured according to ASTM D 570.63, American Standard Type Methods). Thus the film-forming polymers as here contemplated are preferably selected from among such polymers that contain multiple polar structures, e.g. carboxyl and/or ester groups (such as poly(-meth)acrylates), amide groups (such as poly(meth)acrylamides and polyamides), ether groups (such as higher polyethylene- and polypropyleneglycols), completely alkylated polysaccharides (e.g. wholly methylated cellulose etc.), alcoholic groups (e.g. polyvinyl alcohols and polysaccharides, such as starch, optionally in derivatized forms such as hydroxyalkylated and partially alkylated forms, e.g. hydroxypropyl cellulose and methyl cellulose respectively). The decisive factor for the degree of hydrophilicity of a polymer is its content of polar groups. Thus for instance, polymers such as polypropylene, polystyrene etc. have a practically negligible capacity for water adsorption whereas polymers having many closely spaced polar sturctures have significant adsorption values and are more suitable in the context of this invention (film-forming polysaccharides, polyvinyl alcohols etc.). Film-forming polymers based on naturally occurring polymers (biopolymers) as a rule do possess sufficient hydrophilicity.

The exact choice of vehicle in each case will depend on inter alia the test substance and the film carrier employed. The test substance should be homogeneously distributable in the vehicle. The vehicle and film carrier should be chosen such that they will adhere to each other. Hydrophilic test substances (e.g. substances soluble in a polar volatile solvent such as water, ethanol, methanol) will usually require vehicles capable of greater water adsorption (more hydrophilic vehicles) as compared to the cases where hydrophobic test substances are employed which require vehicles that are not solely hydrophilic but additionally have, to some degree, lipophilic properties. As hydrophobic test substances may be mentioned coal tar, balsams and many fragrances. Taking the chemical structure of the test substance as the starting point for his considerations and then carrying out some simple tests the artisan can find the vehicle that is the most suitable one in each individual case. Note that for metal salt and hydrophilic test substances it has been found essential to choose a film-forming polymer capable of forming a film in conjunction with a polar volatile solvent, preferably water, ethanol, methanol etc. or homogeneous mixtures thereof. For these types of test substances, suitable polymers are selected from among film-forming polysaccharides, for example alkylated or hydroxyalkylated cellulose. One such vehicle is partially methylated cellulose; it has a very good hydrophilichydrophobic balance, in addition to possessing very good film-forming properties and being non-irritant on human skin.

The vehicle may consist of a mixture of the above-mentioned polymers; in other words, the vehicle contains at least one of the polymers. A requirement however here is that the mixture has to be capable of giving a film that is swellable when applied occlusively as e.g. in the case of epicutaneous testing.

At the time of the filing date, the best embodiments of the invention were considered to be those employing methylated and hydroxypropylated celluloses according to Examples 2 and 3, resp ..

Important points to consider when selecting the vehicle are that the vehicle should be pharmaceutically acceptable, non-irritant on the skin and inert to the film carrier and that it should not, to any substantial extent, alter the allergenic and/or irritant properties of the test substance.

A liquid is said to be "volatile" if it is capable of evaporating at a temperature at which the test substance employed remains in the film, without destruction of the carrier. As a rule it is possible to employ a liquid having a relatively high vapor pressure at room temperature.

FILM CARRIER

The film carrier may be substantially impermeable to moisture and water, but this is not absolutely necessary. The film carrier should not contain any substances that might give rise to irritation of the skin. Various materials that are suitable in the context of this invention are marketed by a number of companies, such as e.g. plastics papers (Reynolds plastic/coated freezer paper, Reynolds Metal Co., Richmond, Va.), Saran®'brilliant' paper, Saran®'dull' paper (Dow Chemical Co., Midland, Mich.), hydrophobic plastics films (e.g. polyester /Myler®/) and aluminum foil. The choice of film carrier material is not in any way critical to the invention; by simply following the general outlines set forth above the artisan will be able to decide whether or not a given material is suitable for the purpose contemplated. If a moisture-permeable film carrier is chosen, it is important that measures are taken to enable application under occlusion.

MANUFACTURE OF THE TEST PATCH

There are two important steps in the manufacturing procedure which are of prime importance for the result obtained: (1) The test allergen has to be distributed uniformly in the film-forming material. (2) The film carrier has to be coated reproducibly with a film of even thickness. If a hydrophilic vehicle is chosen to be employed on a film carrier which is too hydrophobic in character it may turn out to be difficult to uniformly coat the carrier with the vehicle. In such a case the carrier may be treated so as to be made more hydrophilic. Thus for instance, a polyester film may be treated for a short period of time in an electric field (e.g. corona discharge treatment), or a polyethylene film may be partially oxidized to introduce polar structures.

In accordance with the currently best known method for producing the film the test substance is added to a film-forming polymer (vehicle) dissolved or gelled in a volatile liquid. If the test substance is soluble in the liquid it may be added directly to the mixture containing the polymer. If it is insoluble it may be dispersed or emulsified homogeneously in a finely divided state into the mixture. As an alternative in both of these cases, the test substance may be predispersed in a small amount of a volatile liquid that is miscible with the liquid present in the gel. The film carrier is then coated with a uniform layer of the gel which is then allowed to dry, whereafter this material may be cut into a suitable number of coated patches, these latter being preferably equal in shape and size (area). It may be advantageous to have the coated patches formed with a beveled or rounded edge on their film side. The dried film may have a thickness of e.g. 0.2, 0.1, 0.05 or 0.01 mm depending on the type of coating gel. The area of the coated patches may amount to 0.2–cm². The amount of test substance in the film per unit area thereof will vary according to the type of allergen. Some allergens are more potent than others; the artisan will thus have to carry out some trial and error experimentation in order to find out the suitable effective amount per unit area. In my test, general guideline values may be derived from values earlier found empirically to be suitable for occlusion technique, although it should here be recalled that in the context of the present invention the required amount per unit area may be expected to be lower than those required for occlusion technique work, inasmuch as bioavailability is improved. The term "effective amount per unit area" means the amount of test substance which when employed in the test will cause an allergic or irritative reaction in most of the sensitized or normal individuals. As a rule, the amount of test substance is less than 10 mg/cm², for instance less than 1 mg/cm². In the case of nickel, the effective amount is 0.5 /$\mu$mol/cm² (My test, vehicle: methyl cellulose).

In some cases it may be desirable to determine so-called threshold values for a patient. For this purpose coated patches are prepared which carry different amount/unit area of the same antigen.

The coated patches are then placed onto a pressure-sensitive adhesive skeet material which provides a margin of at least about 5 mm, preferably at least about 1 cm projecting around each coated patch (the film-coated side of each patch being placed so as to face away from the adhesive sheet material). The coated patches are spaced apart with less than 10 cm interstices between them. Their shape is not critical in the context of this invention. Thus as a matter of principle it is possible to employ strips as equivalent to other types of patch shapes.

The adhesive material may be permeable to moisture if the film carrier is impermeable, and should be of a nature such as to gently adapt itself to the skin.

To facilitate the testing procedure, it is possible to prearrange a plurality of coated patches on one common piece of the adhesive material, the individual coated patches having been provided with different allergens each, and/or with the same allergen in different amounts per unit area. With this prearrangement of the coated patches a test strip is obtained with which the patient will be tested simultaneously against a plurality of allergens and/or respectively, against different amounts of the same allergen per unit area. Such strips may comprise coated patches corresponding to a standard tray; each strip may contain up to 25, preferably up to 12 coated patches.

A test strip according to the invention thus consists of a strip of adhesive material ("self-adhesive", pressure-sensitive adhesive material) having on its adhesive face at least one area (=patch) coated with a film with a test substance incorporated therein. The strip may be covered with a protective sheet which is peeled off immediately before use.

For shipping and sale, the strip with its protective sheet may be packaged so as to be hermetically sealed against intrusion of air, moisture, humidity and light, if desired in an inert atmosphere such as a gseous nitrogen atmosphere.

TESTING PROCEDURE

This procedure is carried out in a known per se manner, but employing coated patches according to the present invention. Thus one or a plurality of My test strips (patches applied onto adhesive matieral as aforesaid) are placed on the patient's skin in a manner such that the film will contact the skin in the testing region, whereupon the strip is sealingly pressed against the skin into a fixed position.

The invention will now be illustrated by means of some non-limitative examples.

EXAMPLE 1

As a preliminary experiment, a model substance (methylene blue) was incorpoated in various film-forming vehicles based on cellulose and polyethylene glycol, whereupon these were applied on film carriers and used in accordance with the invention. The film imprints thus obtained revealed a uniform distribution of the model substance, thus showing that the vehicles with suitable film carriers and suitable test substances are useful in the practice of the method of this invention. Methyl cellulose was found to have by far the best film-forming properties; additional experiments were therefore carried out with this cellulose derivative.

EXAMPLE 2

Test material

Cobalt chloride 1 %, nickel sulfate 5 %, potassium dichromate 0.5 % in petrolatum (Hermal-Chemie, Reinbek b. Hamburg, W. Germany).
Finn Chambers ® (Epicon Oy, Finland) on Scanpor ®.
Scanpor ® (Norgesplaster A/S, Norway).
Chemicals:
Cobalt chloride pro analysi, nickel chloride pro analysi, nickel sulfate pro analysi, potassium dichromate pro analysi,
sodium hydroxide pro analysi, dimethylglyoxime, crystalline (Sigma Chemical Co., St. Louis, USA).
Dodecyl sodium sulfate (=sodium lauryl sulfate) technical grade, Matheson Coleman & Bell, Norwood, Ohio, USA).
Methocel ® A4M (methyl cellulose) degree of methylation 27–31 %/glucose unit; Dow Chemical Co., Midland, Mich., USA).
White petrolatum (Hermal-Chemie, Reinbek b. Hamburg, W. Germany).
Plastics foils and plastics-coated papers (film carriers):
Reynolds plastic-coated freezer paper (Reynolds Metal Co., Richmond, VA., USA).
Polyester 0.03 mm (Mylar ®).
Saran ® brilliant 35 CIS/10 SARAN/15 PE, and dull 45 Paper/15 PE (Dow Chemical Co., Midland, Mich., USA).
Six volunteers who were hypersensitive to nickel.

Preparation of test material

Methocel ® gel (3 % w/v) was prepared with the aid of the hot water method (the Methocel ® being stirred up in boiling water; the resultant mixture forms a gel on cooling). Metal salts—crystalline or dissolved in water—were incorporated in the gel. Water was added to a final Methocel> concentration of 2.4 % w/v. Then the gels were stirred thoroughly with a magnetic stirrer until the salts were homogeneously dispersed and dissolved. The gels prior to being applied were centrifuged so that they were then free from air bubbles.

These gels were prepared with the following metal salt concentrations:
Dilution steps (mol/lit.) 0.8, 0.4, 0.2, 0.1, 0.05, 0.025, 0.013, 0.0063, 0.0031, 0.0016, 0.00078, 0.00039, 0.00020, 0.00010 and 0.000049.
$NiCl_2$: 0.8 to 0.000049
$NiSO_4$: 0.2 to 0.000049
$CoCl_2$: 0.2 to 0.0031
$K_2Cr_2O_7$: 0.1 to 0.0031
Dodecyl sodium sulfate (% by weight) 4.0, 2.0, 1.0 and 0.5.

The gels were then spread out as a layer of uniform thickness (about 0.1 mm) on film carries which had been cleansed with ethanol. The gel layer was left to dry at room temperature (giving a film thickness of about 0.01 mm) and was then cut up into square patches, with the aid of a sharp knife.

For comparison purposes a dilution series of nickel sulfate was prepared in that standard patch test material was mixed with petrolatum in twelve dilution steps (5 %, 2.5 %, 1.3 % ... etc., down to 0.0025 % as the twelfth step).

Nickel analysis

Coated Patches (1.0×1.0 cm) carrying films of the 0.1 M nickel sulfate gel on the aforesaid different film carriers were analyzed in series of ten. They were placed into 8 ml of deionized water and sonicated for 1 minute before addition of 12 ml of indicator solution: equal parts of 1.0 N sodium hydroxide in deionized water and 1 % dimethylglyoxime in ethanol. The samples were read four hours later in a spectrophotometer at 470 nm.

Patch test method

Test material with petrolatum/nickel sulfate and coated patches as set forth above were applied onto the upper portion of the back of each individual, this being done with the aid of Finn Chambers ® on Scanpor ® tape or with the aid of Scanpor ® tape alone, respectively, and remained thus affixed for 48 hours. Readings were taken at 48 and 72 hours.

RESULTS

| | Nickel analyses Amount of nickel in four different test papers 1.0 × 1.0 cm with 0.1 M nickel sulfate gel and in 9 to 16 mg samples with 5% nickel sulfate in petrolatum | |
|---|---|---|
| | $\mu$mol Ni | mg $NiSO_4$ |
| Polyester Mylar ® | 0.68 ± 0.06 | 0.180 ± 0.017 |
| Plastics-coated paper | 0.66 ± 0.02 | 0.174 ± 0.006 |
| Saran ® dull | 0.73 ± 0.08 | 0.192 ± 0.021 |
| Saran ® brilliant | 0.71 ± 0.02 | 0.186 ± 0.006 |
| Nickel sulfate, 5% in petrolatum | 2.50 ± 0.61 | 0.660 ± 0.160 |

These results of the nickel analyses show that test materials according to the present invention will give greater dosage precision than could be attained with prior art techniques.

Crystals detectable by microscopic examination were all less than about 90 /$\mu$m in the film plane and all less than about 10 /$\mu$m in the plane perpendicular to the film plane.

Patch tests

Each of the six individuals who were hydpersensitive to nickel (one of them also hypersensitive to cobalt) were patch tested with dilution seris of nickel sulfate in petrolatum and with coated patches according to the invention containing nickel sulfate, nickel chloride, cobalt chloride, potassium dichromate and sodium lauryl sulfate. The coated patches according to the invention were 1 cm² in size. Three persons were additionally tested with nickel sulfate on patches of polyester and Saran® (both 1 cm²). Two persons were tested with 0.7–0.7 cm (0.5 cm²) patches of nickel sulfate on plastics-coated paper.

The test method according to this invention resulted in larger and more evenly distributed test reactions than the test employing Finn Chambers®; this could be seen most clearly in the cases where the coated patches contained the allergen in a much diluted form. The intensity of the test reaction with 5 % nickel sulfate in petrolatum generally corresponded to patches of this invention which contained 0.05 M nickel sulfate gel (0.3 /μmol Ni/cm²). The 0.7–0.7 cm coated patches gave the same intensity of reactions and the same end point of dilution series as did the 1.0–1.0 cm coated patches, but were more difficult to evaluate. The reactions in the test series on polyester and Saran® were identical with those of the paper/plastics series. The person who was hypersensitive to cobalt reacted with equal intensity when tested with 1 % cobalt chloride in petrolatum and when tested with an 0.013 M gel of cobalt chloride on plasticscoated paper. The method of the invention with 0.2 and 0.1 M gels of cobalt chloride and potassium dichromate resulted in irritation reactions equal in intensity to those obtained with 5 to 10 % of these salts in petrolatum (tests carried out on normal persons).

The skin irritant sodium lauryl sulfate when incorporated in a film (0.5–4 %) according to the invention gave irritative reactions corresponding to those obtained in conventional patch testing with this same substance in aqueous solutions (0.25–2 %).

During the time that My coated patches were allowed to remain in their positios as affixed to the test persons the film was observed to swell. This will increase the film-skin contact and presumably facilitate penetration of the test substances into the skin, in that the water-soluble substances will find easier access to the aqueous phase of the skin and the fat-soluble substances will more easily find their way into the lipid phase of the skin. The example shows that a solid, supple film can be used as the vehicle.

Among other test substances that have been incorporated into films Methocel® and successfully evaluated clinically the following may be mentioned:

Neomycin sulfate, ethylene diamine hydrochloride, and balsam of Peru.

EXAMPLE 3

Gels of Klucel® (hydroxypropylated cellulose of Hercules Inc., USA) containing various test substances were prepared, applied on film carriers and allowed to dry, all this in a manner analogous to Example 2. The solvents employed were various mixtures of water and ethanol, the ethanol concentration in each case being sufficient to solubilize the particular test substance employed.

| Type of allergen | Concentration of Klucel® | Concentration of solvent | Concentration of allergen |
| --- | --- | --- | --- |
| Mixture of fragrances | 5.6% | 66% EtOH w/v | 53–0.1 mg/cm³ |
| Colophony | 5.6% | 60% EtOH w/v | 200–2.3 mg/cm³ |
| p-phenylene diamine | 5.0% | 0% EtOH w/v | 6.7–0.01 mg/cm³ |

The film carrier was a polyester film that has been hydrophilized by corona discharge treatment for better adhesion of the film. When the dried film was subjected to microscopy no crystal formation could be detected. The test results obtained on the skin were easy to read.

Among other test substances that have been incorpoated into films of Klucel® and successfully evaluated clinically may be mentioned: nickel sulfate, potassium dichromate, caine mix, balsam of Peru, ethylene diamine hydrochloride, cobolt chloride, thiuram mix and epoxy resins.

Among the substances tested Balsam of Peru and Mixture of Fragrances contain volatile constituents.

EXAMPLE 4

Micronized hydrocortisone acetate (example of a substance of predominantly lipophilic character) slurried in water (10 % w/v) was added to Methocel® gel prepared according to the hot water method. The gel was then, in the form of a film, applied onto plastics-coated paper (according to Example 2). Microscopic examination showed that the hydrocortisone acetate was uniformly distributed in the film.

I claim:

1. In a test strip having at least one patch thereon and intended for use in occlusive epicutaneous testing in order to detect contact allergy, the improvement comprising that a dry film is adhered to one surface of said patch, said film containing as the film-forming substance a film-forming polymer which has incorporated therein a contact allergy test substance and said film-forming polymer being capable of adsorbing moisture from the tested skin area when the test strip is in use.

2. A test strip according to claim 1 wherien said test strip contains a pluraliity of said patches.

3. A test strip according to claim 2 wherein said hydrophilic film-forming polymer on at least one of said plurality of patches exhibits multiple alcoholic groups, or is a hydrophilic film-forming derivative thereof.

4. A test strip according to claim 2 wherein the contact allergy test substance on at least one of said plurality of patches is a metal salt.

5. A test strip according to claim 2 wherein said film-forming polymer on at least one of the said plurality of patches is selected from methylated and hydroxypropylated celluloses and mixtures thereof.

6. A test strip according to claim 2 wherein said film on at least one of said plurality of patches comprises a methylated cellulose.

7. A test strip according to claim 2 wherein said film on at least one of said plurality of patches comprises a hydroxy propylated cellulose.

8. A test strip according to claim 1 wherein the area of said at least one patch is within the range of 0.2–4 cm².

9. A test strip according to claim 1 wherein the thickness of said film is less than 0.25 mm.

10. A test strip according to claim 1 wherein the thickness of said film is less than 10.0 mm.

11. A test strip according to claim 1 wherein said film consists of at least one hydrophilic film-forming polymer.

12. A test strip according to claim 1 wherein said film-forming polymer adsorbs moisture from the tested skin area it swells to a gel.

* * * * *

UNITED STATES PATENT AND TRADEMARK OFFICE

CERTIFICATE EXTENDING PATENT TERM
UNDER 35 U.S.C. § 156

PATENT NO.      : 4,836,217

ISSUED          : June 6, 1989

INVENTOR(S)     : Torkel I. Fischer

PATENT OWNER :  Pharmacia AB

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 899 days from the original expiration date of the patent, June 6, 2006, with all rights pertaining thereto as provided by 35 U.S.C. § 156(b).

I have caused the seal of the Patent and Trademark Office to be affixed this 31st day of May 1996.

Bruce A. Lehman
Assistant Secretary of Commerce and
  Commissioner of Patents and Trademarks